US010213567B1

(12) United States Patent
Theventhiran

(10) Patent No.: US 10,213,567 B1
(45) Date of Patent: Feb. 26, 2019

(54) EASILY REMOVABLE INTUBATING LMA

(71) Applicant: Shan Theventhiran, Staten Island, NY (US)

(72) Inventor: Shan Theventhiran, Staten Island, NY (US)

(*) Notice: Subject to any disclaimer, the term of this patent is extended or adjusted under 35 U.S.C. 154(b) by 0 days.

(21) Appl. No.: 15/807,572

(22) Filed: Nov. 8, 2017

(51) Int. Cl.
A61M 16/00 (2006.01)
A61M 16/04 (2006.01)
A61B 1/267 (2006.01)

(52) U.S. Cl.
CPC ......... A61M 16/0409 (2014.02); A61B 1/267 (2013.01); A61M 16/0434 (2013.01); A61M 16/0488 (2013.01); A61M 2210/0625 (2013.01)

(58) Field of Classification Search
CPC .......... A61M 16/0409; A61M 16/0434; A61M 16/0488; A61M 2210/0625; A61B 1/267
See application file for complete search history.

(56) References Cited

U.S. PATENT DOCUMENTS

| 4,069,820 | A | | 1/1978 | Berman |
| 4,509,514 | A | | 4/1985 | Brain |
| 4,693,243 | A | | 9/1987 | Buras |
| RE35,531 | E | | 6/1997 | Callaghan |
| 5,937,859 | A | | 8/1999 | Augustine |
| 5,937,860 | A | | 8/1999 | Cook |
| 6,070,581 | A | * | 6/2000 | Augustine ............... A61B 1/267 128/200.26 |
| 6,095,144 | A | * | 8/2000 | Pagan ................... A61M 16/04 128/207.14 |
| 6,422,239 | B1 | | 7/2002 | Cook |
| 6,427,686 | B2 | | 8/2002 | Augustine |
| 6,439,232 | B1 | | 8/2002 | Brain |
| 7,134,431 | B2 | | 11/2006 | Brain |
| 7,493,901 | B2 | | 2/2009 | Brain |
| 8,215,307 | B2 | * | 7/2012 | Nasir ................... A61M 16/04 128/200.26 |
| 8,820,319 | B2 | | 9/2014 | Schwartz |
| 2002/0112728 | A1 | * | 8/2002 | Landuyt ................ A61M 16/04 128/207.15 |
| 2006/0254594 | A1 | | 11/2006 | Gologorsky |
| 2014/0378770 | A1 | | 12/2014 | Dhonneur |
| 2016/0008562 | A1 | | 1/2016 | Sagales Manas |

FOREIGN PATENT DOCUMENTS

EP 2258431 8/2010

* cited by examiner

Primary Examiner — Steven Douglas
(74) Attorney, Agent, or Firm — Joshua Kaplan; Kaplan Law Practice, LLC

(57) ABSTRACT

Supraglottic airway devices such as the laryngeal mask airway (LMA) device are used in anesthesia practice to maintain an open airway in patients undergoing anesthesia. LMA devices are also used as a conduit for the insertion of endotracheal tubes (ETT) through the laryngeal opening into the patient's trachea (endotracheal intubation). In scenarios where the conventional method of tracheal intubation is challenging or not possible, modified LMA devices have played a pivotal role for several decades. However, present embodiments of LMA devices suffer from significant shortcomings that the device in this patent aims to address. Currently available modified LMA devices have many limitations when used as a conduit for the insertion of ETT. The apparatus shown the present description aims to address those major limitations and to significantly improve the success rate of tracheal intubation.

16 Claims, 14 Drawing Sheets

EASILY REMOVABLE INTUBATING LMA

FIELD OF THE INVENTION

The present invention relates to supraglottic airway devices such as laryngeal mask airway (LMA) devices. In particular, to the role of LMA devices as a conduit to facilitate the fiberoptic bronchoscope (FOB) guided insertion of an endotracheal tube (ETT) into the trachea (endotracheal intubation).

BACKGROUND OF THE INVENTION

An LMA has been in use as an anesthetic administration device for several decades and is described in the U.S. Pat. Nos. 4,509,514; 6,422,239; 5,937,860; and 2,205,499. A standard LMA device is comprised of an airway tube and an elliptical shape mask with an inflatable cuff. An inflation line is attached to the outer aspect of the cuff to inflate or deflate the cuff with air. The distal end of the airway tube is attached to the back of the mask with an opening into the mask. This mask part of the device is then inserted into the pharyngeal cavity via the mouth of a patient under anesthesia. The cuff is inflated via the inflation line to create an adequate seal between the mask and the soft tissue of the pharynx. This mask sits above the vocal cords, such that the concave cavity of the mask is level with the laryngeal opening to maintain the patient's airway. The proximal end of the airway tube is outside the oral cavity, and is connected to an anesthesia breathing circuit to deliver oxygen and anesthetic gas mixture to facilitate anesthesia and maintain breathing during a surgery.

LMA devices have the disadvantage of not providing a complete seal of the airway; therefore, they are not the airway device of choice in patients who are at risk of aspiration, patients at risk of regurgitation of stomach contents into the trachea and lungs, or patients who need a complete seal of the airway for mechanical ventilation of the lungs. The endotracheal tube (ETT) is the preferred and most effective airway device for this group of patients. The ETT comprises a flexible tube with an inflatable cuff near the distal end and an inflation line that is attached to the cuff to inflate and deflate the cuff. Endotracheal intubation (ETI) comprises insertion of the ETT into the trachea through the laryngeal opening. Upon insertion, the cuff rests below the vocal cords and it is subsequently inflated with air via the inflation line to seal the trachea and provide protection against the passage of regurgitated stomach contents into the lungs. The proximal end of the ETT sits outside the mouth and is attached to the anesthesia circuit to deliver oxygen and anesthesia gas mixture to maintain anesthesia and ventilation of the patient. It can alternatively be connected to a mechanical ventilator to mechanically ventilate critically ill patients.

ETI is often performed via the aid of a procedure called laryngoscopy. This entails using a laryngoscope to view the vocal cords and laryngeal opening and subsequently insert the ETT into the trachea. The conventional methods of ETI can be difficult or impossible in some patients. In this subcategory of patients, a fiberoptic bronchoscope (FOB) is used to visualize the laryngeal opening to intubate the trachea with the ETT. This is a more skilled procedure and requires a conduit to guide the FOB and ETT to achieve successful endotracheal intubation. Since the cuff of the LMA in the patient's pharynx faces the laryngeal opening, the LMA is used as a guide to FOB visualization of the vocal cords, larynx and trachea. The FOB can thus be manipulated to pass through the laryngeal opening into the trachea. A well lubricated ETT is then threaded over the FOB in the trachea.

However, using the LMA device as a conduit has multiple limitations which diminish the success rate. Multiple modifications of LMA devices have been described in US patents over the past several decades (U.S. Pat. No. 4,509,519). Some of the past modifications to the LMA device have attempted to address the devices limitations. However, each solution introduced its own shortcoming, which in turn prevented these solutions from approval or widespread acceptance. There are two major problems with the LMA as a conduit for FOB guided endotracheal intubation:

(1) The ETT cuff is bulky, which makes its insertion into the airway tube of the LMA and subsequent threading of it through the airway tube into the trachea is challenging. Therefore, most of the time a smaller ETT is utilized, which is not ideal if long term ventilation is needed.

(2) LMA devices cannot be left in the patient for a prolonged period due to the risk of pressure injury to the soft tissue in the pharynx. To avoid pressure injuries, an LMA must be removed after the ETT is threaded into the trachea. However, the chance of dislodging the ETT during the LMA's removal remains high, since all existing LMA designs require the LMA being pulled out of the pharynx over the ETT.

The invention addresses all the major limitations in this conduit technique and potentially provides a significant improvement in the success rate of ETT insertion and removal of the LMA after the ETT is in place, making it a near ideal conduit for FOB guided endotracheal intubation.

SUMMARY OF THE INVENTION

The present invention is a laryngeal mask airway (LMA) assembly that is comprised of structural elements that significantly improve the safety and utility of current existing LMA intubation technology while eliminating the major limitations of the use of current LMA devices for fiberoptic bronchoscopy guided intubation.

The LMA device embodied in the present invention (FIG. 4) is comprised of a split airway tube along its length with a wider opening closer to the distal end. The cuff of the mask contains a split that corresponds to the split along the distal airway tube. An expandable membrane 190 covers (FIG. 2) the device from the outer part of the split cuff (193) to beyond the airway tube (192). This expandable membrane helps to thread a larger size ETT in the airway tube 20 as the wider opening in the airway tube accommodates the cuff of the ETT. The expandable membrane can also be split open along the length of the membrane by pulling the ribbon 270-280, which will enable easier removal of the LMA from the ETT without dislodging it.

A soft flap (200) is attached to one side of the split cuff and covers the gap by resting against the other side of the split cuff. This feature will prevent any air leak through the gap 181 when the patient is ventilated.

The final product of using the apparatus disclosed in the present invention is shown in FIG. 1. In this intubation technique, an endotracheal tube (ETT-140) is inserted into the airway tube 20 of the LMA device 10. The cuff 145 of the ETT140 sits at the level of the wider opening 300 of the airway tube 20 and the tip 142 of the ETT 140 is just inside of the airway tube 20 of the LMA device 10. This unit is inserted into the pharynx 130 of the patient under anesthesia and once in place, both cuffs (LMA 110 and ETT145) are inflated through their respective inflation lines (326, 146). A sealing adaptor (swivel connector) 400 is attached to the proximal end 143 of the ETI 140 and an anesthesia circuit is attached to the other end of the swivel connector 400; this allows oxygen to be administered throughout the intubation procedure. The fiberoptic (FOB) scope 141 is then threaded through the opening on the top of the swivel connector 400 and upon visualization of the vocal cords and laryngeal opening 320, the tip 141 of the FOB is passed into the trachea 132 (FIG. 9). Then the expandable membrane 190 of the LMA is split open along its full length from 193 to 192 by pulling the ribbon 280 which is attached distally 270 to the membrane 190. Now both cuffs (ETT and LMA) are deflated through their respective inflation lines. The ETT 140 is then threaded downwards, without any resistance, into the trachea 132 over the FOB 141 via the split-open LMA airway tube 20. The FOB 141 is then removed leaving the ETT 140 in place. The ETT cuff 145, which is resting in the trachea, is then re-inflated. The anesthesia circuit (not shown in the diagrams) is then attached to the proximal end 143 of the ETT 140 to deliver oxygen and anesthesia gas mixture to the patient. The correct position of the ETT 140 is confirmed by auscultation and capnography.

It is one objective of the present invention to create a new and safer LMA device.

It is another objective of the present invention to provide a variably expanding LMA device.

It is still another objective of the present invention to have a flap to cover an expandable gap of an LMA device.

Yet another objective of the present invention is to create an easily removable device that is capable of being peeled off of an endotracheal tube and any scoping equipment; leaving such devices undisturbed during the LMA removal process.

DESCRIPTION OF THE PREFERRED EMBODIMENTS

Figure 1:
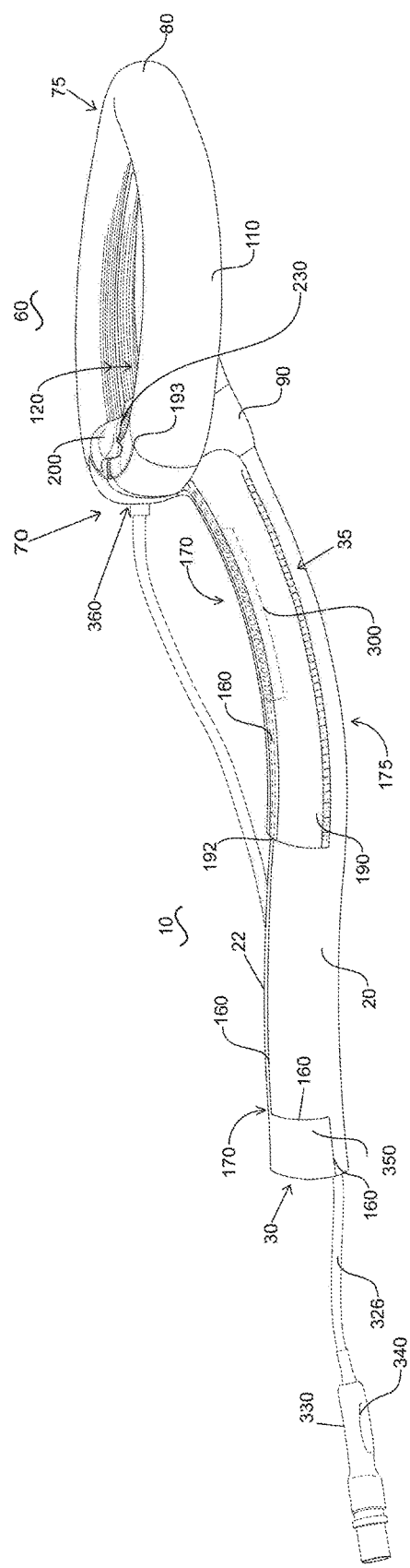
FIG. 1 is a close-up side view of the apparatus embodied in the present invention.

The preferred embodiments of the present invention will now be described with reference to the drawings. Identical elements in the various figures are identified with the same reference numerals.

Reference will now be made in detail to embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

The main objective of the present invention is to create a device that significantly improves the safety and utility of current existing laryngeal masked airway (LMA) intubation technology while eliminating their major limitations with regards to fiberoptic bronchoscopy guided intubation.

The present invention is a significantly modified LMA assembly with the solution expressed in an expandable corpus of the flexible airway tube to allow use of a larger and appropriately sized endotracheal tube (ETT) without difficulty and also being easily removable by splitting open the airway tube without dislodging the ETT after the intubation process is completed. This modification also helps to effectively deliver oxygen and anesthetic gas mixture during the intubation process, reduces the potential of patient soft tissue injury and decreases the risk of possible damage to the reusable fiberoptic bronchoscope.

Figure 2:
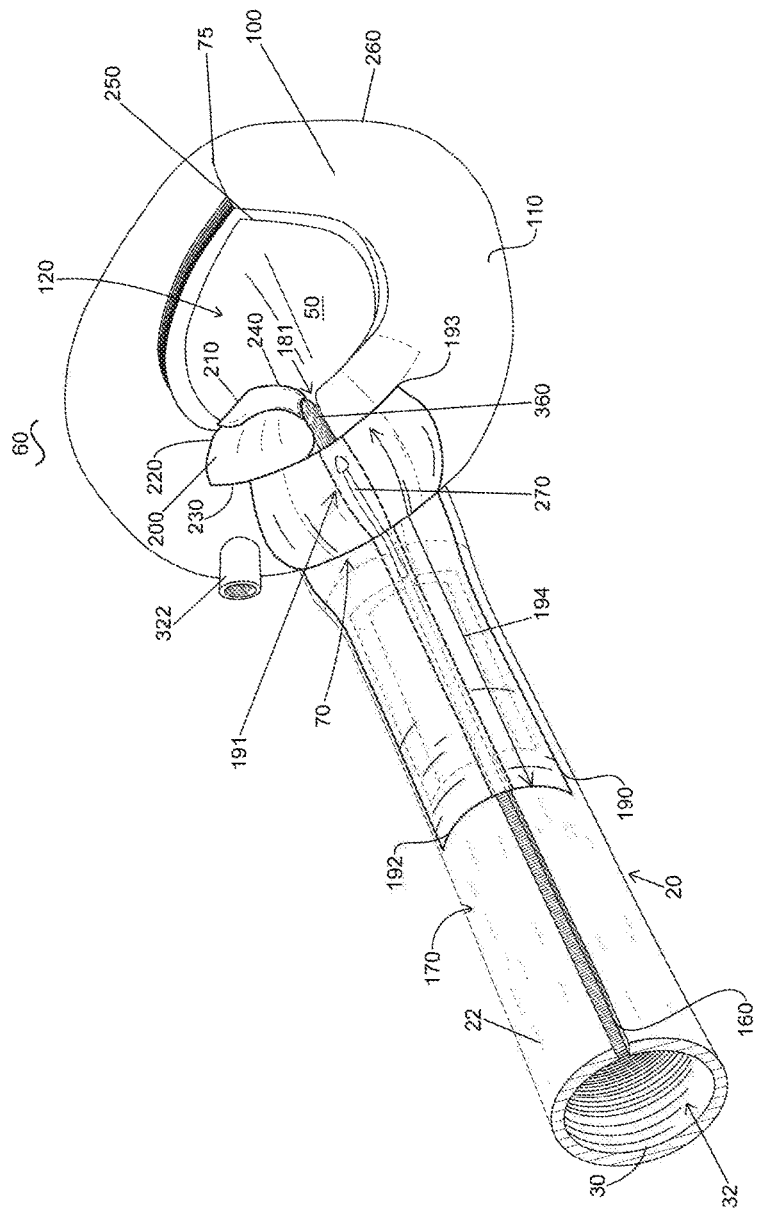
FIG. 2 is a close-up of the fissure line with a direct view at the bottom of the invention
Figure 3:
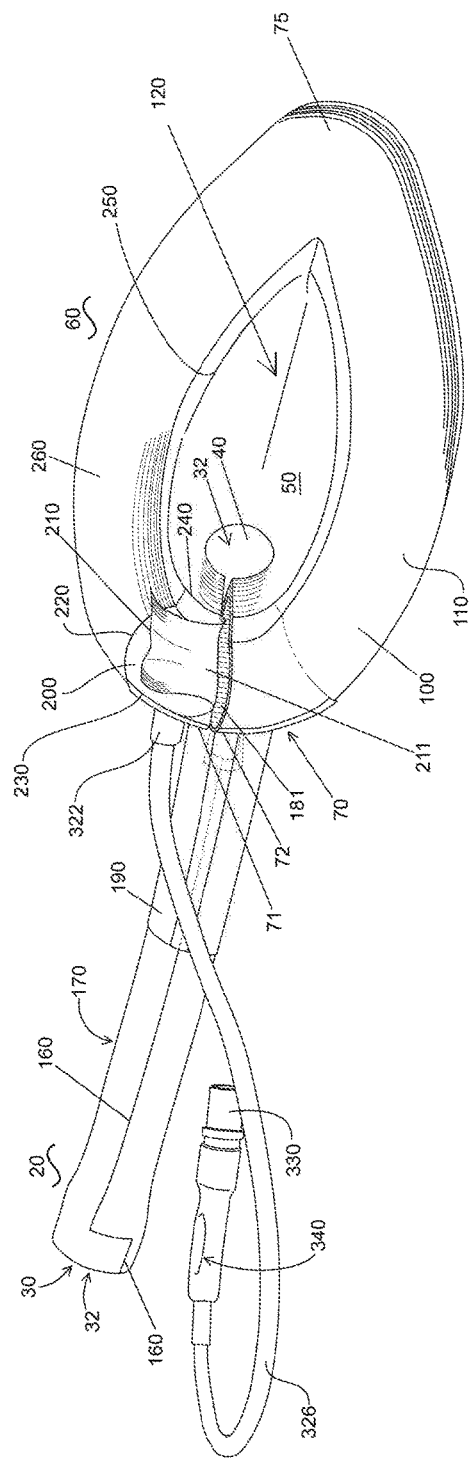
FIG. 3 is a direct view at the bottom of the device embodied in the present invention, with a direct view at the elastic membrane.

Turning now descriptively to the drawings, in which similar reference characters denote similar elements through the serial views; FIG. 1, FIG. 2, and FIG. 3, show an airway assembly 10, a flexible airway tube 20, a proximal aperture 30, a mask 60, a proximal end 70, a distal end 75, a point on said cuff 110, a point of coupling 90, an orifice 120, a fissure line from the proximal to distal end of the airway tube 160, a bottom side 170, an elastic membrane 190, a flap 200, a proximal edge 230, a surface of said cuff 260, a distal ribbon 270, a proximal end of said ribbon 280 (FIG. 5), a window 300 (FIG. 4), an inflation balloon 340, an inflation line 326, connected to an external valve 330, a side section 350. The cuff 110 with the rim 100 is uniform throughout, despite the presence of the flap 200 that covers the gap 181.

In FIG. 1 the airway assembly 10 is shown with the flexible airway tube 20 firmly connected to the mask 60 at the point of coupling 90. The airway tube 20 is made of material that is sufficiently flexible to allow it to fit into a patient's airway passage and also firm enough to maintain the shape of the inner diameter of the airway tube. Polyvinyl chloride (PVC) or any other flexible material approved for use with these devices are made for single use.

FIGS. 1, 2 and 3; the distal end of the airway tube is connected to the back of the mask 60 with a point of coupling 90 and the distal aperture 40 open in the concave cavity 50 of the mask 60. When this mask is in the oropharynx, the cuff 110 is inflated via the inflation line 326 to create an adequate seal between the cuff and the soft tissue of the pharynx. The mask sits in front of the vocal cords and the concave cavity 50 of the mask and the distal aperture 40 of the airway tube faces the laryngeal opening. The airway tube 10 contains the proximal aperture 30 through which the endotracheal tube (ETT) and fiberoptic bronchoscope (FOB) can be inserted into the airway tube 32.

The window 300 is a substantial rectangular cutout along the sidewall 22 (FIG. 4) that forms the bottom side 170. The opening of the window depends on the diameter of the airway tube. In an adult size LMA the window opening is approximately 4 to 7 cm lengthwise (33) by 2 to 3 cm side to side (34). The purpose of the window 300 is to provide for a slightly larger space to accommodate the ETT cuff 145 (FIG. 5) when it is inflated inside of the airway tube 20 of the LMA. The stretchable membrane 190 covering the fissure 160 and the window expands and accommodates larger ETT 140 and its cuff 145. This stretchable membrane gives way when the ETT is threaded into the lumen 32 of the airway tube 20 to maintain the integrity without rupturing. It can be split open only with a vertical pull by the ribbon 280 when the time comes to remove the LMA after the ETT 140 is inserted into the trachea 132.

The elastic membrane 190 has significant surface integrity to be capable of significant flexibility without ripping or tearing. The elastic membrane 190 is preferably made out of highly ductile materials such as resin, PVC or silicone. It may further contain embedded interconnected elastic strips to improve surface integrity and strength without compromising its pliability. The proximal end 192 of the elastic membrane 190 is shown to begin at approximately midpoint along the bottom 170 of the flexible airway 20. Alternatively, the proximal end 192 may extend to the side section 350 and even to the proximal aperture 30. The elastic membrane 190 straddles the fissure line 160, to keep the fissure line 160 from rupturing prematurely, while inserted devices are still being threaded along the hollow channel formed by the airway tube 20. The fissure line 160 is shown in FIG. 1 beginning at the proximal end 30 and running in a virtual straight line along the entire length of the bottom side 170. The fissure line 160 shifts to the side in a close proximity to the proximal aperture 30, creating the side section 350. The purpose of the side section 350 is to alleviate irritation caused by edges of fissure line 160 on parts of the oral cavity. Furthermore, to avoid triggering premature rupture of the fissure line 160 due to closing of a person's bite, the fissure line is moved to the side in section 350.

The ability of the airway assembly 10 to be completely split open is a major improvement of the present invention over devices that presently exist in the art. FIG. 2 shows a split fissure line 160, the elastic membrane 190, the proximal end 192 and the distal end 193 of the elastic membrane 190, and the flap 200. Also shown in FIG. 2 are the proximal aperture 30, the bowl 50, the mask 60 a proximal end 70, a distal end 75, the cuff 110, the orifice 120, the bottom side 170, the elastic membrane 190, and the flap 200. With respect to the flap 200, FIG. 2 also demonstrates the right end 210, the left end 220, the proximal edge 230, the distal edge 240, the base of the cuff 250, the surface of the cuff 260, the distal part of the ribbon 270, and a tube 322 for attaching an inflation line 326 to inflate the cuff 110.

The fissure line 160 represents the section of the surface area 22 of the flexible airway 20 that can be easily opened due to the presence of a perforation on the covering elastic membrane 190 by only the vertical pull of the distal ribbon 270 and ribbon 280. The fissure line 160 is a pressure line or fault line, which tends to create a more delicate connection than the surrounding surface, causing it to be more predisposed to tearing than the surrounding area. It is preferable that the fissure line 160 is completely closed while being inserted into a patient because the structures of such a device will lack structural integrity and will buckle at the slightest push force that is necessarily present during the insertion process. The fissure line 160 extends from the proximal end 30, in essentially a straight line, until the gap 181, in the ring of the cuff 110. Alternatively, the fissure line 160 may run on a diagonal along the bottom surface 170.

The elastic membrane 190 may be attached to the surface area 22 adhesives on both edges and left loose in the middle for yielding of the fissure 160 under the membrane to accommodate a larger size ETT 140 when it is threaded through the lumen 32 of the airway tube 20. It may also be a unitary part of the flexible airway assembly 20. FIG. 2 shows that the elastic membrane 190 rests along the bottom side 170 of the device 10 in essentially a straight line, with the proximal end 192 located in a close proximity with the proximal aperture 30, and a distal end 193 located on the rim 100 of the cuff 110. It is preferable that a single, uninterrupted segment of the elastic membrane 190 is utilized given that a single uninterrupted segment of elastic may be stronger than multiple disconnected sections. Alternatively, the elastic membrane may be formed from multiple segments of an elastic membrane. Multiple disconnected sections are better suitable in avoidance of premature split of the fissure line 160, since only small segments will become split at any given time. The ribbon 270 that extends for the entire length of the elastic membrane 190 may still be able to split the fissure line 160 in a single pull notwithstanding the plurality of sections. Alternatively, the membrane covering the airway tube 20 and part of the cuff 191 can be split with two separate ribbons. The distal end of 193 of the elastic membrane 190 is on the rim 100 of the cuff 110, and is adjacent to the proximal edge 230 of the flap 200. The flap 200 is a strip of a highly pliable material which is the same as the rest of the device. It is attached to the surface 260 of the cuff 110 with only one end. In FIG. 2 the left end 220 is attached to the surface 260, while the right edge 210 is loose and is firm enough to fold over the right side of the cuff 260 to completely cover the gap 181 in the proximal cuff 360, which when inserted into the patient's pharynx prevents air leak.

The flap 200 is mounted with its distal edge 240 essentially adjacent to the base of the cuff 250, and the proximal edge 230 being adjacent to the distal end 193 of the elastic membrane 190. In this orientation, the flap 200 is mounted on the inside of the cuff 110, directly facing the bowl or the orifice 120. The flap 200 is predisposed to assume an essentially flat profile along the surface 260, which would cover the gap 181. When inserted into the patient's pharynx, the flap 200 is held in a flat position, covering the gap 181 while the airway assembly 10 is being inserted into a patient. This result is achieved since this section of the cuff 110 receives the brunt of friction against the epiglottic structures while the mask 60 is being pushed into place. This friction keeps the flap 200 essentially flat at all times, unless the mask 60 is being pulled out, in which case the pull force will tent to curl the flap 200 away from the surface area 260, as shown in FIG. 2.

As shown in FIG. 2, flexible airway 20 contains a hollow channel 32 that begins at the aperture end 30 and runs the entire length of the flexible airway 20. The air to inflate or deflate the cuff 110 may enter and exit through the inflation line 326. The gap 181 may be partially or completely squeezed shut once the cuff 110 is fully inflated. The membrane 190 covering the split part of the cuff 193 will help both edges of the split cuff maintain a closed position to prevent any air leaks. In such circumstance, the cuff 110 would be made of soft but ductile material that will give way and accommodate the contours of the epiglottic structures, yet be sufficiently ductile to achieve a flash seal all around the laryngeal opening.

FIG. 3 is a detailed diagram of the mask 60. The cuff 110 surrounds the orifice 120. The base of the orifice is the bowl 50. The bowl 50 is the underside of the dome of the mask 60 to which the flexible airway 20 connects. Also shown in this figure is the distal aperture 40, which is the exit point of the hollow tube 32 formed by the flexible airway tube 20. The gap 181 divides the proximal end 70 of the cuff 110, and extends up to the distal aperture 40. The flap 200 is shown rolled up with the right side 210 folded over the left side 220.

It is preferable that one side of the flap 200 is attached to the surface 260 of the cuff 110, while the rest of the length of the flap 200 is loosely stretched over the surface 260, thereby covering the gap 181. The underside 211 of the flap 200 may contain a light adhesive or at least frictional elements to improve adhesion to the surface 260 as long as the right edge of the flap 210 is resting in a flat profile over the gap 181.

The gap 181 form a narrow passage between two terminal points 71 and 72 of the cuff 110. There may or may not be any actual separation between terminal points 71 and 72. However, due to the presence of the gap 181, it is preferred that the terminal points 71 and 72 do not share the same terminating sidewall. As shown in FIG. 3, the flap 200 is attached to the first terminal point 71, with the rest of the flap 200 being long enough to cover the gap 181 and the second terminal point 72. The flap 200 is preferably placed between the base of the cuff 250 and the rim of the cuff 100. The flap 200 may also extend into the bowl 50 until the distal aperture 40. Also shown in FIG. 3 are the proximal aperture 30, which is the starting point for the hollow tube 32, the fissure line 160, the bottom side 170, the elastic membrane 190, the distal end of the inflation line 322, the external sleeve for the inflation line 326, the bottom side 170, the external valve 330, through which the cuff 110 is inflated when it is in the patient's pharynx to form a seal around the laryngeal opening and the distal aperture 40 faces the laryngeal opening.

Figure 4:
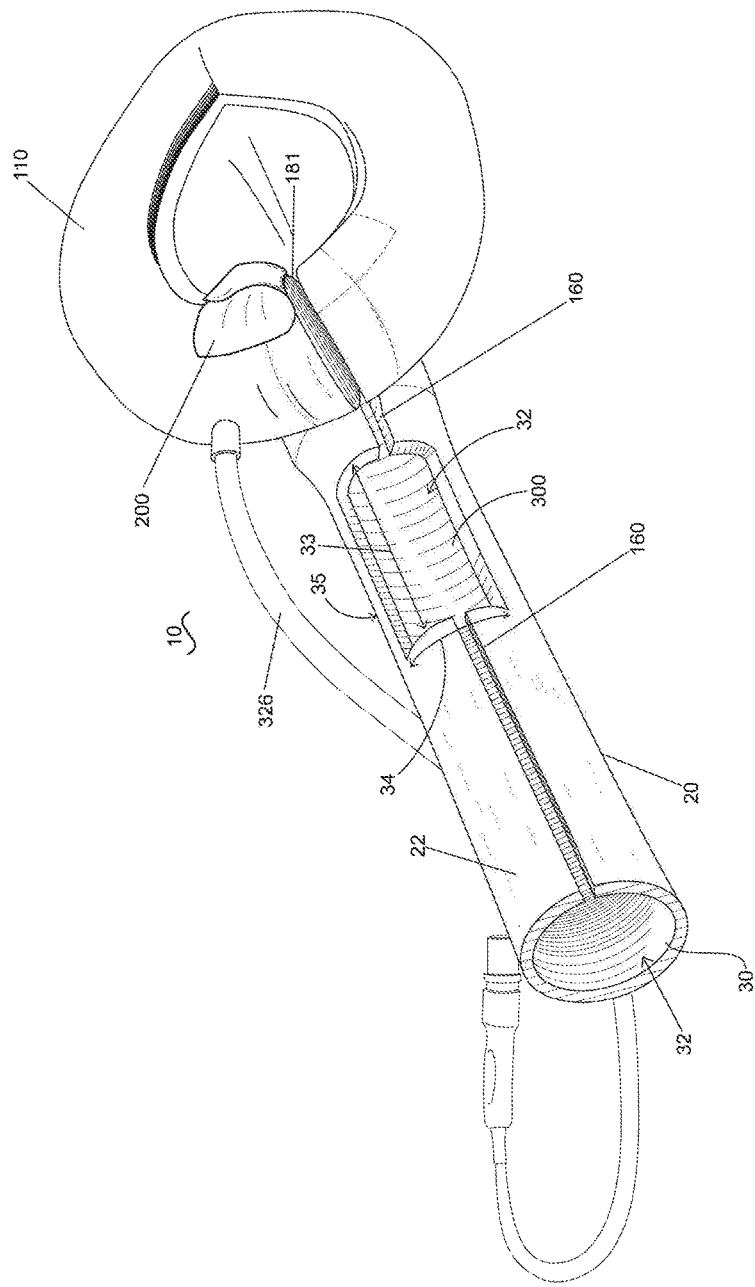
FIG. 4 is another side view of the present invention with window exposed for review.

The flexible airway tube 20 shown in FIG. 4 without the elastic membrane 190; exposed is the window 300 that corresponds to the bend 35 to provide additional space to maneuver ETT 140 being passed through the hollow tube 32. The preferred length of 33 of the window 300 may be up to 4-7 cm in an adult size LMA and the width of the arch 34 may be up to 2-3 cm. Alternatively, the window 300 may be longer or shortened according to the size of the LMA. The fissure line 160 on the flexible airway 20 corresponds to the gap 181 on the cuff 110, so that the airway assembly 10 may be peeled off the ETT 140 held within the hollow tube 32.

Figure 5:
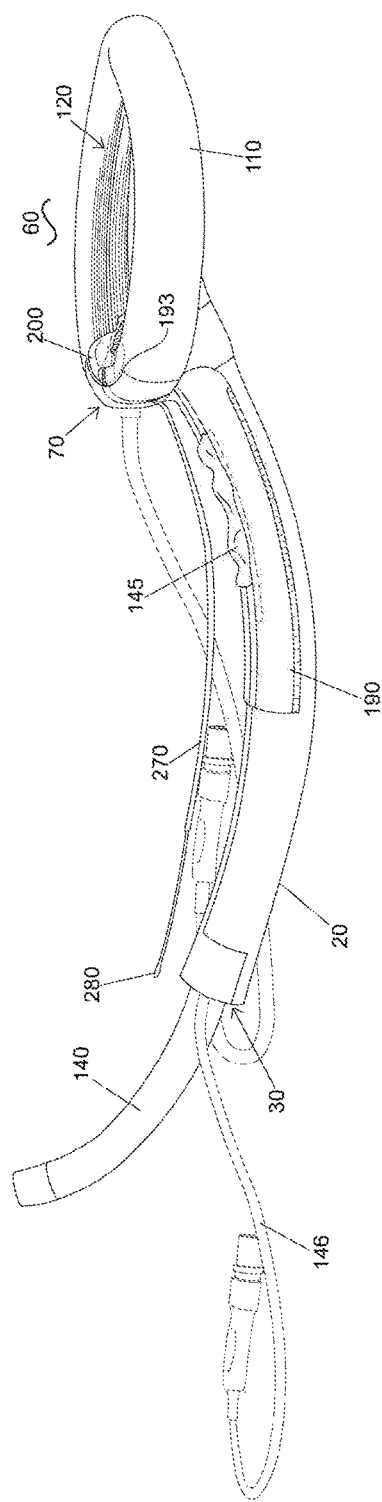
FIG. 5 is a side of the present invention demonstrating the ribbon.
Figure 6:
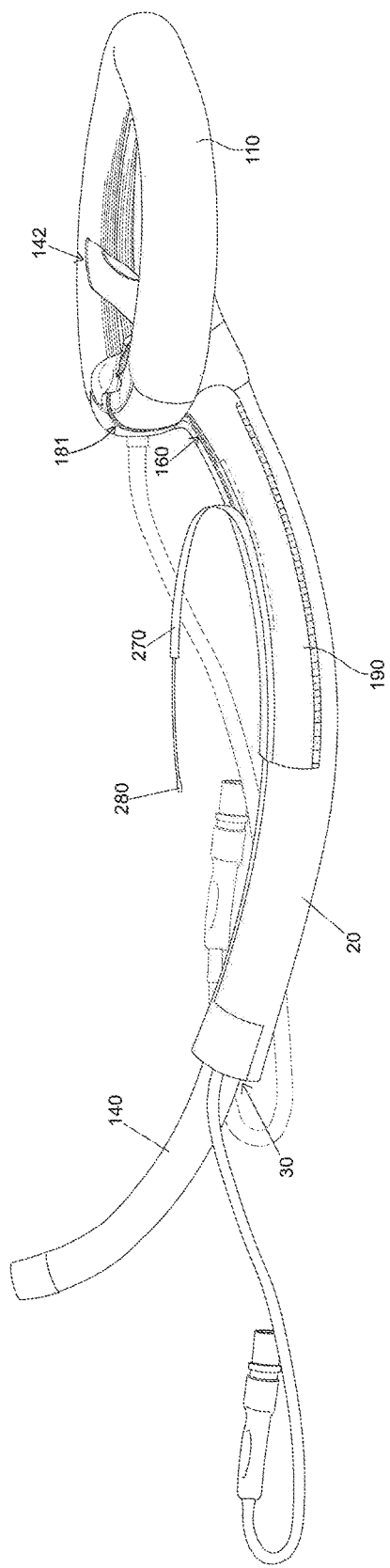
FIG. 6 is a side of the present invention demonstrating the ribbon being partially activated.
Figure 7:
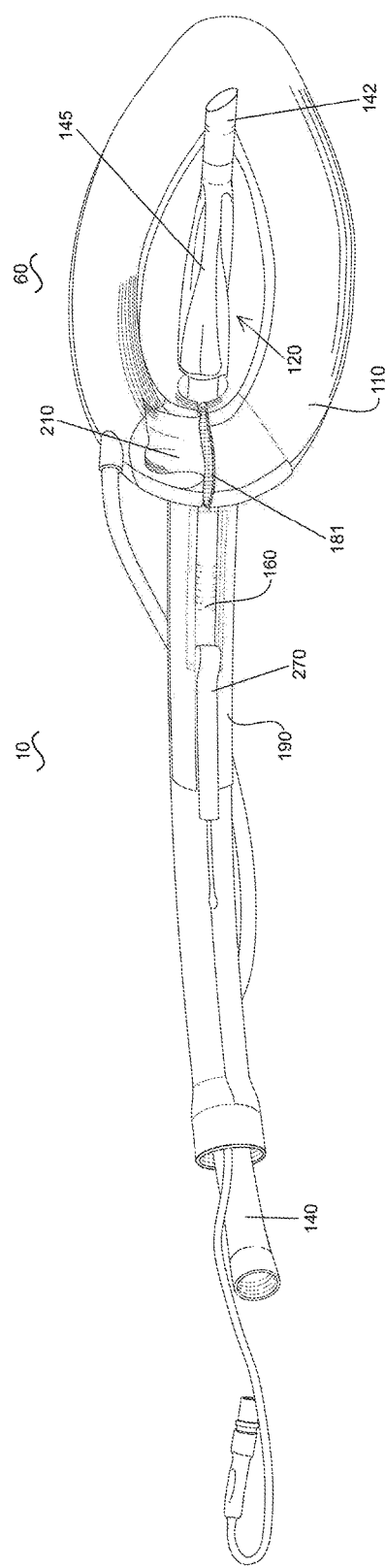
FIG. 7 is a view of the bottom side of the present invention demonstrating the ribbon being partially activated.

FIGS. 5 through 7 demonstrate the utility of the present invention when coupled with the intended use of being a conduit for delivery of ETT 140 and scoping tools 141. Shown are the mask 60, the flexible airway tube 20, the elastic membrane 190, the flap 200, the cuff 110 and the orifice 120. The elastic membrane 190 is shown having a ribbon 270, with the proximal end 280 of the ribbon 270 extending back toward the proximal aperture 30. The ribbon 270 is preferably mounted on the elastic membrane 190 at the distal end 70 of the cuff 110 (FIG. 2). The endotracheal tube 140 is shown inserted through the proximal aperture 30 into the lumen 32 of the airway tube 20. The cuff 145 of the ETT 140 sits underneath the membrane 190 at the level of the window 300 of the airway tube 20.

FIG. 6 demonstrates the tripping of the ribbon 270 initiated by the proximal end 280, which opens the gap 181 on the cuff 110. Pulling the ribbon towards the proximal aperture 30 continues the tearing of the elastic membrane 190, which in turn causes the splitting of the fissure line 160. FIG. 6 also illustrates the forward end 142 of the ETT 140 that has been passed through the flexible airway tube 20.

The tripping action of the ribbon 270 is further demonstrated with a frontal close-up diagram in FIG. 7 showing the ribbon 270 being partially peeled along the length of the elastic membrane 190, revealing the gap 181 and the fissure 160, both of which are now split. The flap 200, which has been partially covering the gap on the cuff 110 can be easily moved out of the way and therefore does not require to be split. The forward end 142 of the ETT 140 has now completely moved through and past the mask 60, with the cuff 145 of the ETT 140 exposed just outside the orifice 120, which would be in the vicinity of the laryngeal opening 320

Figure 8:
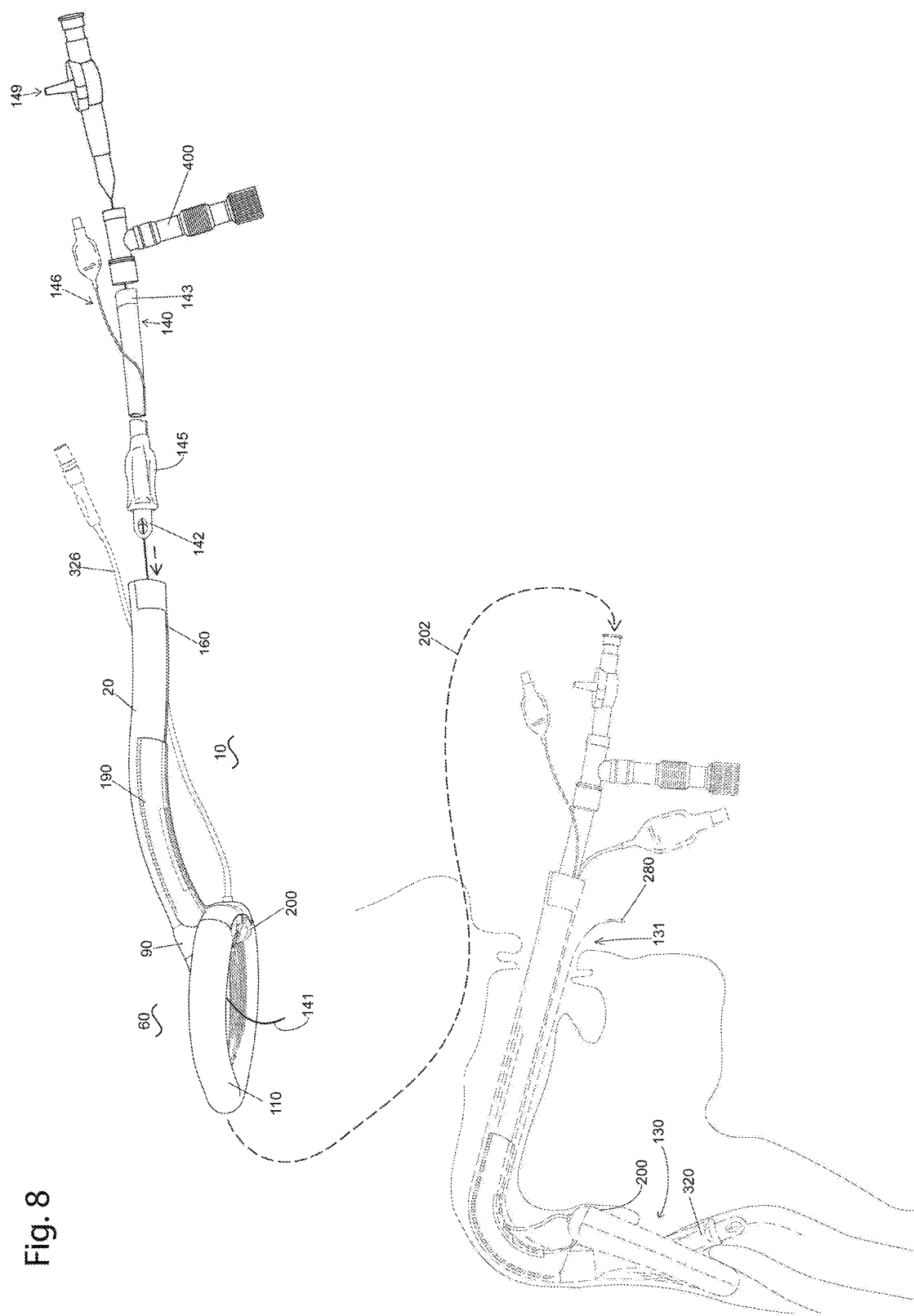
FIG. 8 demonstrates usage of the present invention.

FIG. 8 demonstrates the components used in fiberoptic bronchoscope guided endotracheal intubation. The invention 10 is a significantly modified LMA device (please see FIGS. 1, 2 and 3 for the details of invention 10) and other components (not part of inventions) needed for the intubation process are a endotracheal tube (ETT) 140, a resealing adaptor (swivel connector) 400, and a fiberoptic bronchoscope (FOB) 149 with the control end 149 and the flexible tubular 141 extension of the FOB.

Description of Fiberoptic Bronchoscope (FOB) Guided Intubation Via the Invention—a Modified LMA Device 10 Acting as a Conduit for the ETT 140 and FOB 141

Figure 9:
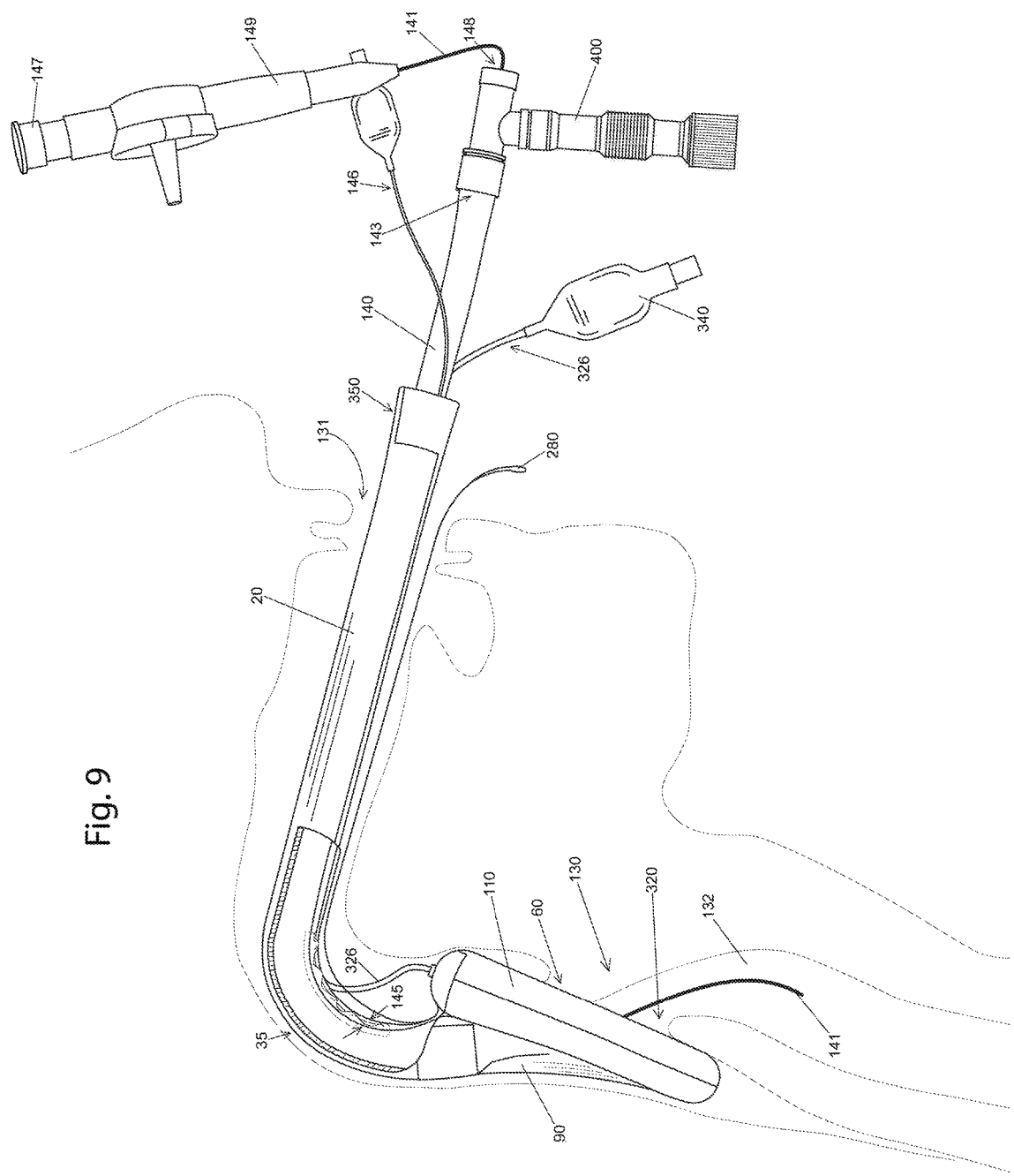
FIG. 9-FIG. 13 are cutaway diagrams of the present invention during and after intubation, and during various stages of removal of the present invention after intubation.
Figure 10:
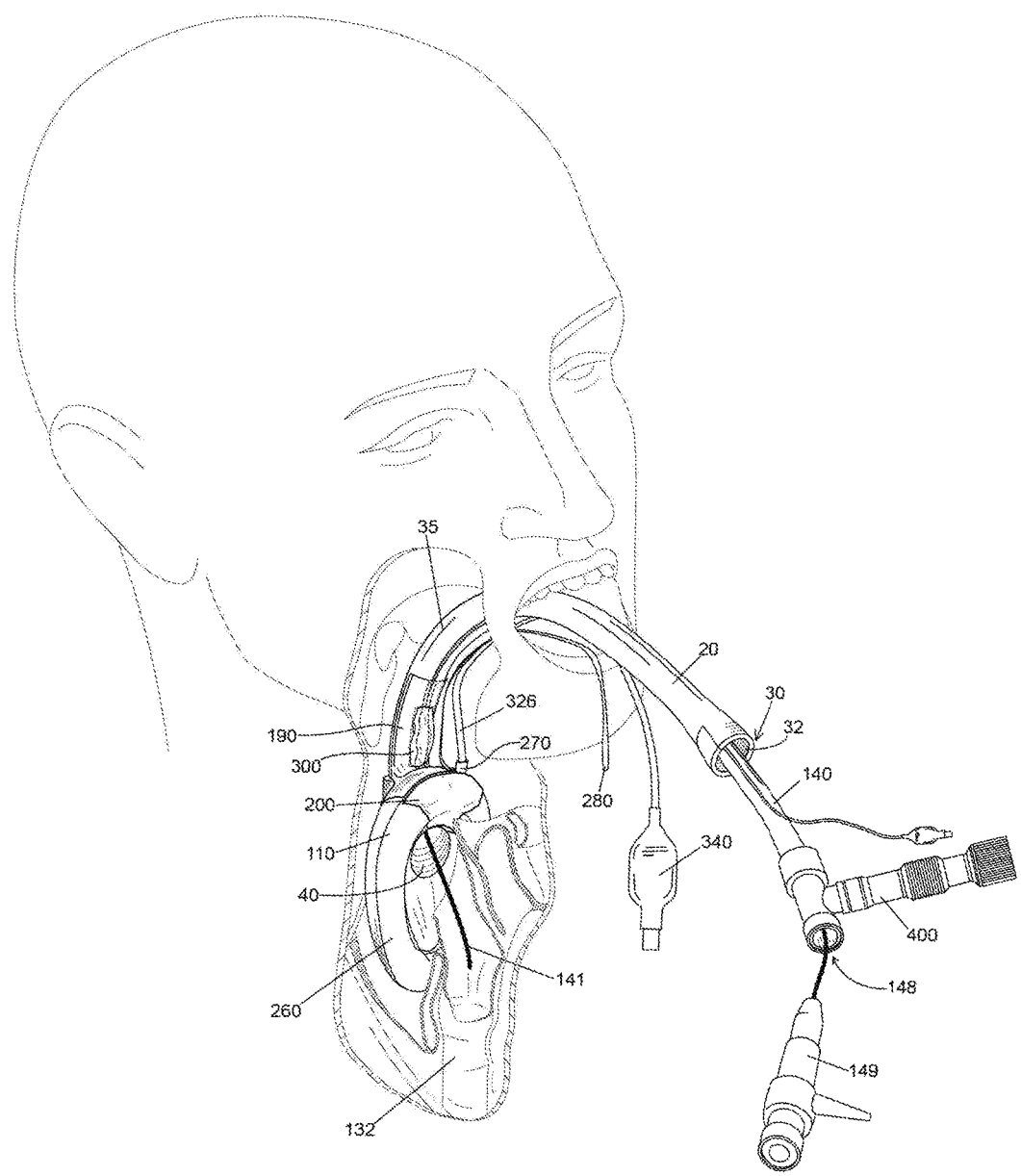

FIGS. 1, 5, 8, 9, 10. The final product of the invention is a modified LMA device 10 as shown in FIG. 1. In this intubation technique, the ETT 140 is threaded into the airway tube 20 of the LMA device 10 via the proximal aperture 30 while the cuff 145 of the ETT 140 is in the deflated state. When positioned in the airway tube 20, the tip 142 of the ETT 140 sits just inside the distal aperture 40 of the airway tube 20 and the cuff 145 of the ETT 140 is at the level of the window opening 300 of the airway tube 20 underneath the membrane. This unit (ETT 140 and LMA device 10) is now inserted through the oral-cavity 131 into the pharynx 130 of the patient under anesthesia. This curved and flexible tube 20 and the mask 60 follow the airway passage of the patient and the distal end 80 of the cuff 110 reaches a point where it no longer can be pushed further and the mask opening 120 is shaped to fit close to and facing the laryngeal opening 320 (FIG. 9). Once this unit is in place both LMA cuff 110 and the ETT cuff 145 are inflated via their respective inflation lines 326 and 146 (FIG. 9). The inflated ETT cuff 145 is still in the airway tube 20 at the level of the window opening 300 and creates a seal inside the airway tube 20. The inflated LMA cuff 110 creates a seal against the pharyngeal soft tissue and, as shown in FIG. 8, the flap 200 is pressed flat over the gap 181 and rests on the right side of the cuff 110 of the mask 60 between the pharynx 130 soft tissue and the cuff 110 and therefore prevents air leak when the patient is ventilated with oxygen and anesthesia gases. Once these cuffs are inflated and the unit is in place, a swivel connector (resealing adaptor) 400 is attached to the proximal end 143 of the ETT 140 and an anesthesia circuit (not shown on the diagram) is connected to the other end of the swivel connector 400; thereby allowing oxygen and anesthesia gases to be administered via this assembly throughout the intubation process. This allows adequate time for the operator to complete this intubation process. FIGS. 9 and 10; once the ventilation is established, the distal flexible part 141 of the FOB 149 is inserted through the resealable opening 148 on the swivel connector 400 and then passed through the proximal end 143 of the ETT 140. It is subsequently passed through the entire length of the ETT 140, while the operator is looking through the eyepiece 147 of the FOB 149, and upon visualization of the vocal cord and the laryngeal opening 320 the tip of the flexible part is 141 advanced into the trachea 132 (FIG. 9).

FIGS. 9 and 10: please note the window 300 of the airway tube 20 of the LMA device 10 (FIG. 8). The inflated cuff 145 of the ETT 140 inside the distended membrane 190 demonstrates the utility of the window 300 in providing additional space within the lumen 32 of the airway tube 20 and further demonstrates the utility of the expandable elastic membrane 190. Please note also the flap 200 on the gap 181. Also note the proximal end 270 and the distal end 280 of the ribbon outside the oral cavity 131. The inflation line 326 to the cuff 110 of the LMA device and the inflation line 146 to the cuff 145 of the ETT 140. The distal aperture 40 of the airway tube 20, opens inside the mask 60 and faces the laryngeal opening 320 (FIG. 8). The flexible part 141 of the FOB is in the trachea 132 (FIGS. 9 and 10).

FIG. 9 shows the final position of the components of the assembly. The airway tube 20 and cuff of the LMA device 10 (the invention). The ETT 140 is in the airway tube 20. The swivel connector 400 is connected to the proximal end 143 of the ETT 140 and the other end of the swivel connector 400 is connected to the anesthesia circuit (not shown). The FOB 149 with the eyepiece 147 and the flexible part 141 enters the resealing opening 148 of the swivel connector 400 and proximal end 143 of the ETI 140 and has passed through the ETT and enters through the mask 60 of the LMA device and into the trachea 132.

Figure 11:
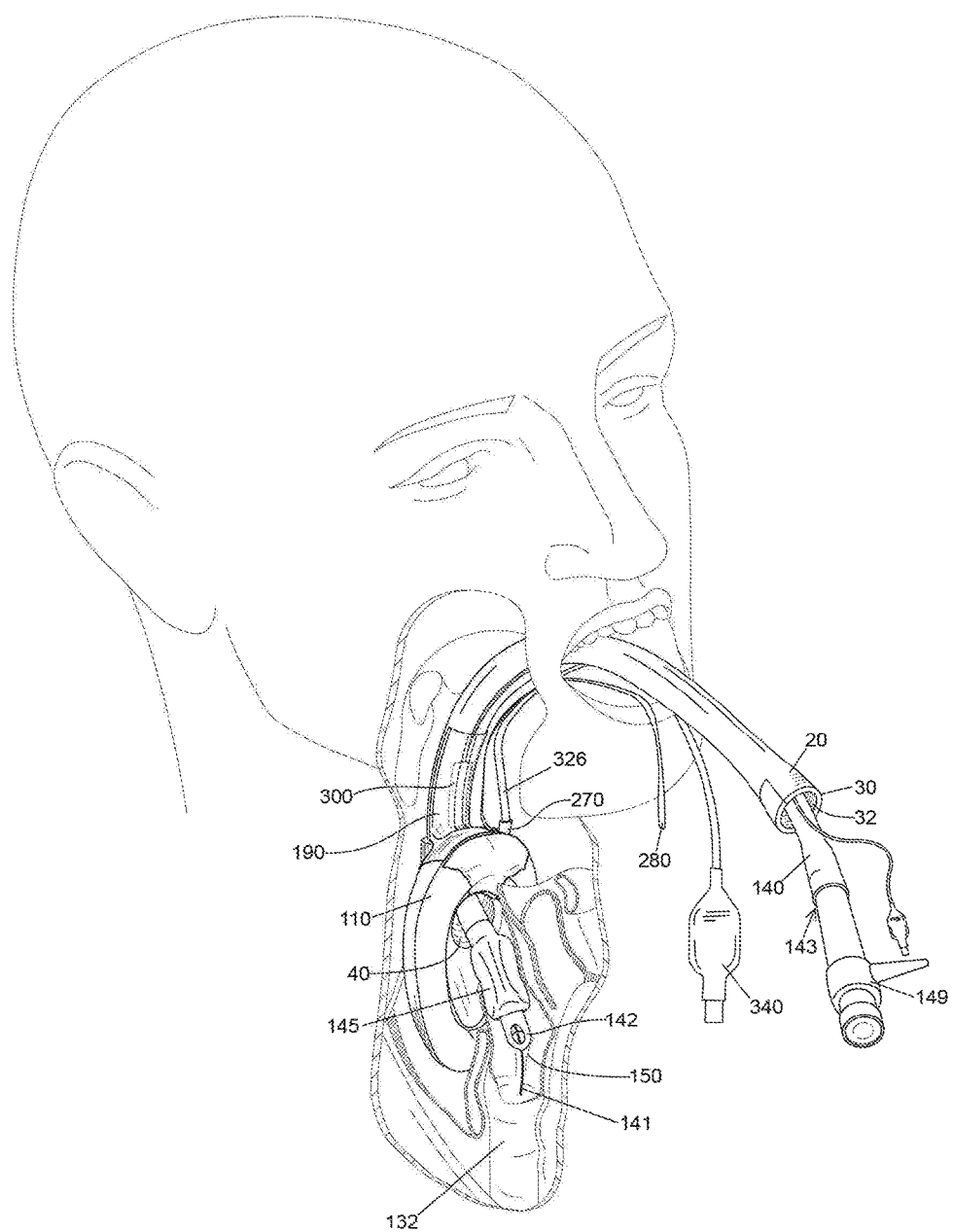

FIG. 11 shows the airway assembly with all structures firmly in position. The cuff 145 of the ETT 140 is deflated at this point and slightly advanced through the distal aperture 40 of the airway tube 20 and through the laryngeal opening 320 and just into the trachea 132 (the swivel connector is not shown in FIG. 11). The ribbon 270 is still intact. The membrane 190 over the window 300 has now resumed a shape uniform to the rest of the airway tube 20 as the cuff 145 of the ETT 140 is moved out of that window 300 area into the laryngeal opening 320.

The next phase of this intubation process is to advance the ETT 140 further down the trachea, at least 3 to 5 cm to the final position in the trachea 132, and successfully remove the LMA device 10 without dislodging the ETT 140 from the trachea 132. These are the two main limitations, in anesthesia and critical care practice, found with the use of laryngeal mask airway (LMA) devices of the prior art. This present invention is a significantly modified LMA device which is designed to overcome these two shortcomings in FOB assisted endotracheal intubation, firstly by easily allowing for the advancement of the ETT 140 into the final position in the trachea 132 of the patient, avoiding the difficult step of pushing the ETT 140 against the high resistance of the airway tube of LMA devices of the prior art. Secondly, this device is easily removed from the pharynx and oral cavity by slipping off from around the ETT 140 without dislodging it by splitting open the membrane 190 of this airway device. These two features will significantly improve the success rate of the intubation process and may reduce the risk of soft tissue injury to the patient and risk of damage to the expansive reusable FOB 141 by avoiding the pulling and pushing involved in these two steps.

Figure 12:
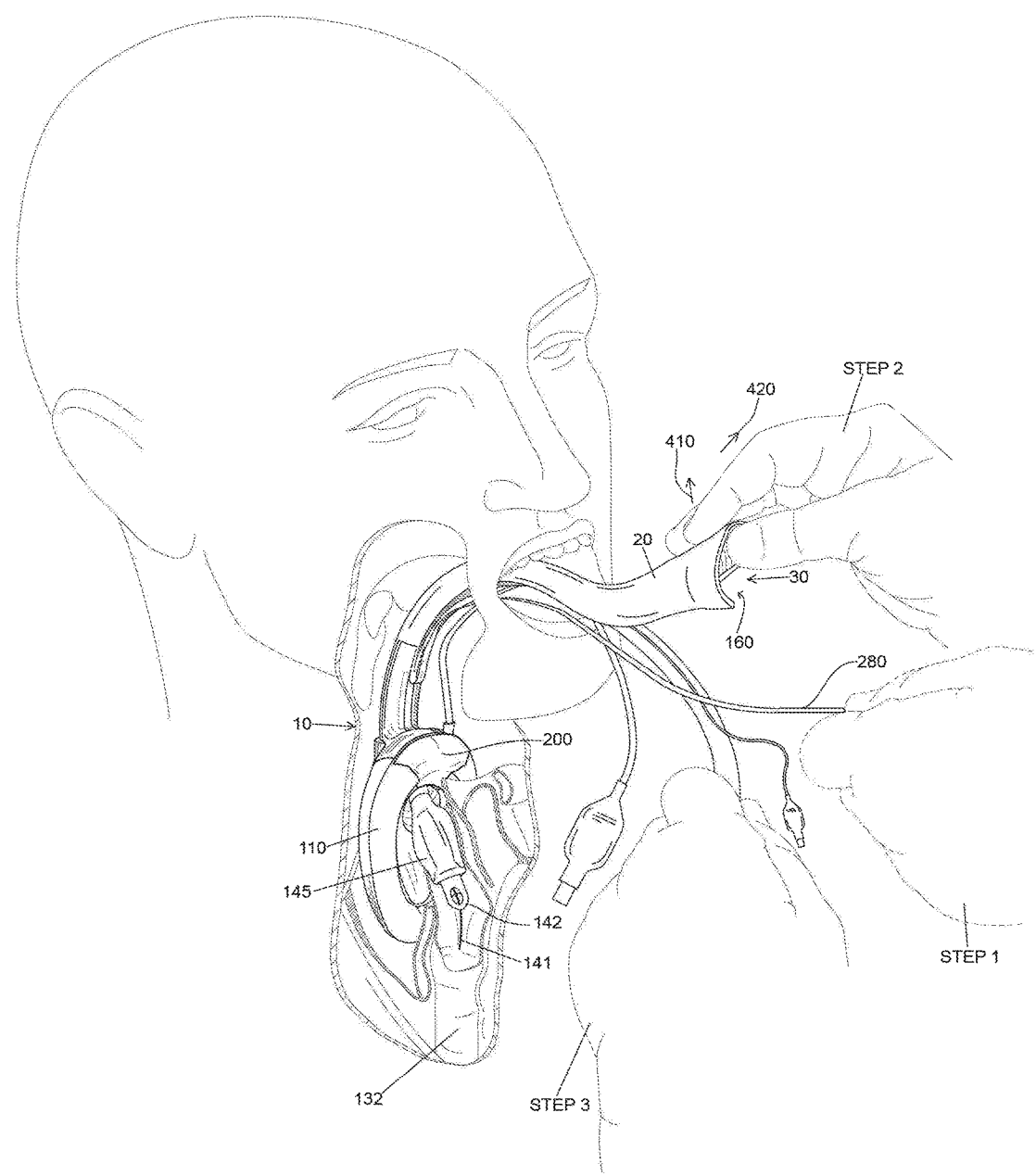
Figure 13:
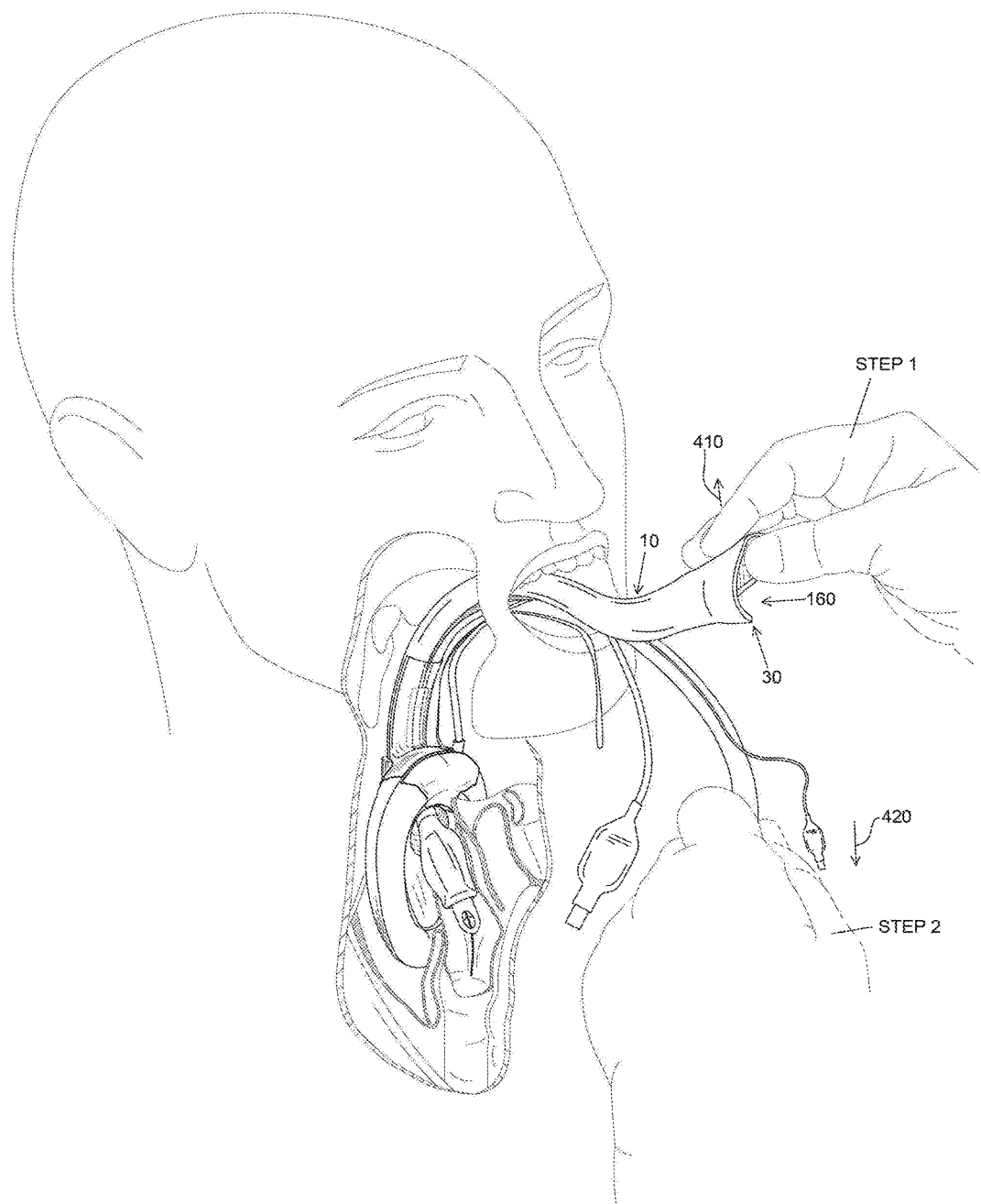

These two features are demonstrated in the next intubation process with FIGS. 12 and 13. In this phase the airway device 10 is being removed and the ETT 10 remains in the patient's trachea 132. FIG. 12: step 2 and 3, the first operator holds the assembly unit (the LMA device 10 and ETT 140) firmly in position and in step 1, the second operator initiates the split of the membrane 190 (on the cuff 110 and airway tube 20) by pulling on the distal end of the ribbon 280. The split is initiated at the cuff 110 where the distal end of the splitting ribbon 270 is attached (see FIGS. 2, 6 and 7). The split starts from the line 193 on the proximal outer rim of the cuff 110 and continues to split the membrane 190 over the airway tube 20 up to the point 192 and reopens the fissure line 160 and also the split 181 in the cuff 110 (FIG. 6). Since the cuff already contains the gap 181, it will be slipped off from around the ETT 140, given the fissure line 160 is completely split all along the length of the flexible airway tube 20. The flap 200 will not serve as an impediment to the removal of the cuff from and around the ETT 140 since it loosely abuts the cuff 110 and may be lifted with minimal effort to remove the ETT 140 from within the flexible airway tube 20 and the mask 60.

Figure 14:
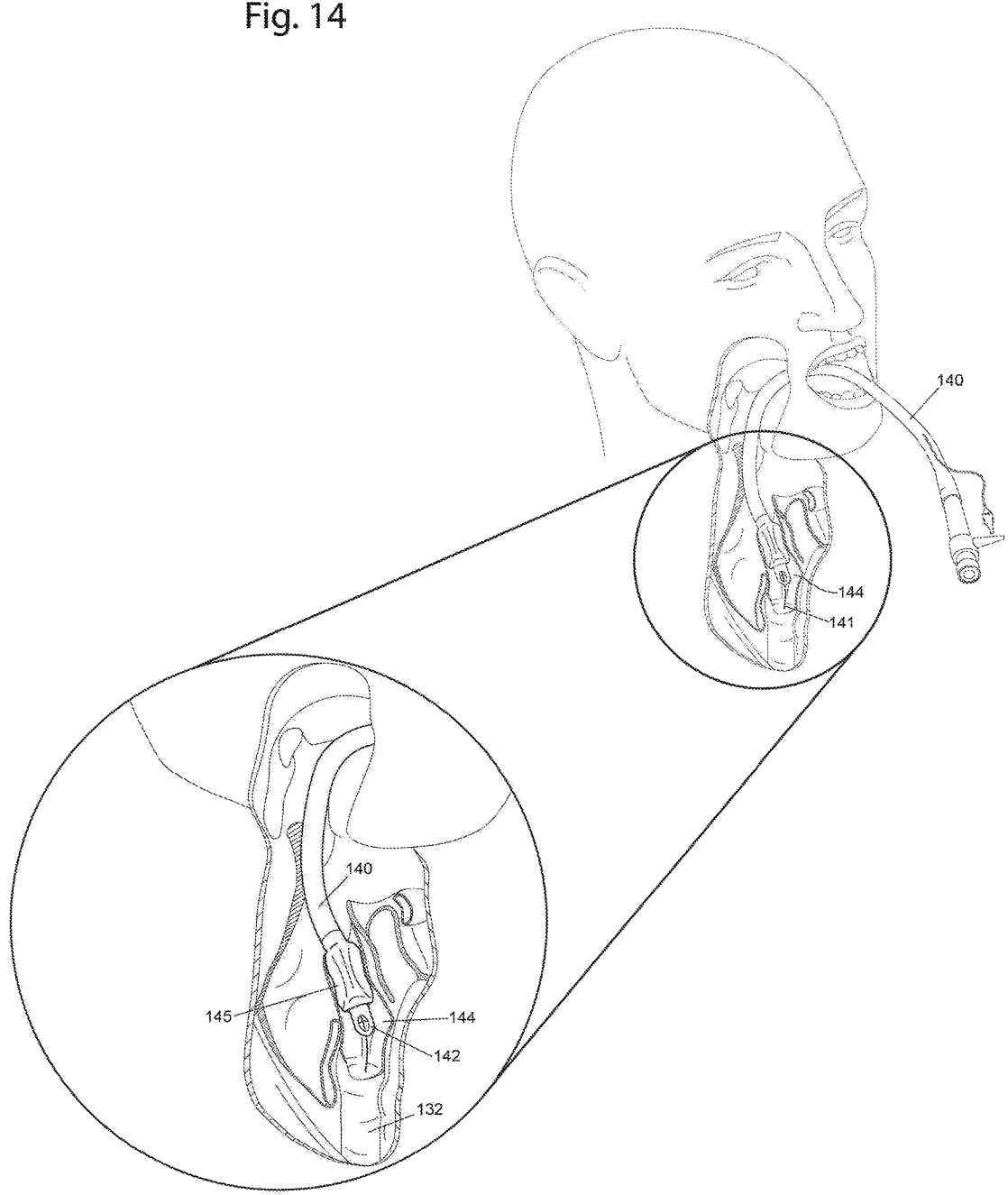
FIG. 14 demonstrates the positioning of the ETT upon removal of the LMA.

FIG. 13 further demonstrates the removal process of the split open LMA device. It demonstrates separating the airway device 10 from the ETT 140 in a 2-step maneuver. In step 1, there is upward 410 lifting of the split open LMA device 10. In step 2, the ETT 140 is simultaneously pulled downwards 420 while firmly holding it to avoid moving the distal end of 142 of the ETT 140 from the trachea 132. Then finally the LMA device 10 is removed from the pharynx (this is not shown in the diagram) by pulling the airway device 10 backwards and outwards; thereby, essentially separating the airway device 10 and ETT 140 apart and then pulling the airway device 10 from the pharynx 130 and finally, through the oral outlet 131. Now the distal end 142 of the ET 140 and the distal end 141 of the FOB 149 are still in the trachea 132 as shown in FIG. 14. Then the ETT 140 is further advanced into the trachea 132 to the desirable length over the FOB flexible tube 141. Alternatively, the ETT 140 is advanced further into the trachea 132 before pulling the LMA device 10. Once the ETT 140 is correctly placed in the trachea 132, the FOB flexible tube 141 is then removed leaving the ETT 140 in place. The ETT cuff 145 which is resting in the trachea 132, is then re-inflated. The anesthesia breathing circuit is attached the proximal end 143 of the ETT 140 to deliver the oxygen and anesthesia gas mixture. The correct position of the ETT 140 is confirmed by auscultation and capnography.

Although the apparatus disclosed in the present application has been described with a certain degree of particularity, it is to be understood that the present disclosure has been made only by way of illustration and that numerous changes in the details of construction and arrangement of parts may be resorted to without departing from the spirit and the scope of the invention.

What is claimed:

1. An airway assembly comprising: a flexible airway tube having a proximal aperture and a distal aperture; said distal aperture coupled with a bowl of a mask having a proximal end and a distal end; a rim of said mask forming a cuff, said cuff surrounding an orifice of said bowl; wherein said bowl and cuff adapted to conform to a patient's supraglottic structures; a proximal end of said cuff being adjacent from said distal aperture and said distal end being a point on said cuff furthest away from said distal aperture; wherein a point where said distal aperture coupled with said bowl of said mask is located is substantially closer to said proximal end of said mask; said flexible airway tube having a hollow channel beginning from said proximal aperture and terminating at said distal aperture, wherein said distal aperture opening into said orifice, said hollow channel being a conduit for an endotracheal tube and scoping tools threaded through said hollow channel into said orifice; a fissure line disposed on a bottom side of said flexible airway tube originating from said proximal aperture until said proximal end; said fissure line of said flexible airway tube continuing in a substantially straight line over said proximal end of said cuff; said fissure line held closed with an elastic membrane; and wherein said elastic membrane capable of sustaining a degree of expansion before splitting along said fissure line; a flap having a right and left ends and a proximal edge and a distal edge; wherein said fissure line passes beneath said flap in between said right end and said left end; wherein said distal edge disposed adjacent to a base of said cuff facing said orifice and said proximal edge reaching a rim of said cuff; and wherein said right end or said left end of said flap permanently attaching to a surface of said cuff and wherein an unattached end of said flap loosely covering said fissure line.

2. The airway assembly of claim 1, wherein a distal end of said elastic membrane further extends to substantially cover said fissure line on said cuff.

3. The airway assembly of claim 2, wherein said proximal edge is laid adjacently to said distal end of said elastic membrane.

4. The airway assembly of claim 3, wherein said proximal end of said cuff further comprises a gap corresponding to the fissure line on said flexible airway tube.

5. The airway assembly of claim 1, wherein said elastic membrane further comprises a ribbon disposed on said fissure line, a forward end of said ribbon extending substantially beyond a distal end of said elastic membrane to function as a pull-string for tearing said elastic membrane along said fissure line.

6. The airway assembly of claim 1, wherein said flexible airway tube further comprises a window, said window intersecting a length of said fissure line, said window admitting said endotracheal tube being tunneled through said hollow channel.

7. The airway assembly of claim 5, wherein said flexible airway tube further comprises a window, said window intersecting a length of said fissure line, said window admitting a laterally expanding inflation balloon of said endotracheal tube.

8. The airway assembly of claim 1, wherein said cuff is capable of being inflated through an airline connected to an external valve.

9. The airway assembly of claim 1, wherein said fissure line shifts to a side section of said elastic airway tube at a point when said fissure line is substantially at said proximal aperture, such that a patient being intubated by said airway assembly biting down on a section of said conduit that is not interrupted by said split.

10. A removable intubation device comprising: a flexible airway tube having a proximal aperture and a distal aperture; said distal aperture coupled with a bowl of a mask having a proximal end and a distal end; a rim of said mask forming a cuff, said cuff surrounding an orifice of said bowl; wherein said bowl and cuff adapted to conform to a patient's supraglottic structures; a proximal end of said cuff being adjacent from said distal aperture and said distal end being a point on said cuff furthest away from said distal aperture; wherein a point of where said distal aperture coupled with said bowl of said mask is located substantially closer to said proximal end, said cuff having first and second terminal ends at said proximal end, wherein said terminal ends each comprising of a terminating sidewall, wherein said sidewall of each said terminating sidewall remaining adjacent to each other when said cuff is inflated; wherein said flexible airway tube having a hollow channel beginning from said proximal aperture and terminating at said distal aperture, wherein said distal aperture opening into said orifice; wherein said hollow channel serving as a conduit for an endotracheal tube and scoping tools are threaded through said hollow channel into said orifice; a fissure line disposed on a bottom side of said flexible airway tube originating from said proximal aperture until said proximal end; said fissure line of said flexible airway tube continuing in a substantially straight line over said proximal end of said cuff; said fissure line held closed with an elastic membrane; and wherein said elastic membrane capable of sustaining a degree of expansion before splitting along said fissure line; a flap having a right and left ends and a proximal edge and a distal edge; wherein said fissure line passes beneath said flap in between said right end and said left end; wherein said distal edge disposed adjacent to a base of said cuff facing said orifice and said proximal edge reaching a rim of said cuff; and wherein said right end or said left end of said flap permanently attaching to a surface of said cuff and wherein an unattached end of said flap loosely covering said fissure line of said cuff.

11. The removable intubation device of claim 10, wherein said proximal end of said cuff further comprising a gap corresponding to said fissure line of said flexible airway tube, said gap completely splitting said cuff at said proximate end, said gap continuing through said bowl until said distal aperture.

12. The removable intubation device of claim 10, wherein said flexible airway tube further comprises a window, said window intersecting a length of said fissure line, said window admitting laterally expanding tubes disposed within said hollow channel.

13. The removable intubation device of claim 10, wherein said cuff is inflatable and further comprising an airline that is inflated through an external valve, said external valve having a safety pilot balloon for detecting uninflated cuff.

14. The removable intubation device of claim 10, wherein said fissure line shifts to a side section of said elastic airway tube at a point when said fissure line is substantially at said proximal aperture, such that if a patient being intubated with said removable intubation device bites down on a section of conduit that is not interrupted by said split.

15. The removable intubation device of claim 10, further comprising a tear-away ribbon disposed at a patient insertion end of said elastic membrane, and a pull-string for activating said tear-away ribbon.

16. The removable intubation device of claim 15, wherein said elastic membrane is longitudinally expandable without activating said tear-away ribbon.

* * * * *